(12) United States Patent
Roberts

(10) Patent No.: US 11,613,529 B2
(45) Date of Patent: Mar. 28, 2023

(54) CRYSTALLINE FORM OF 6-(CYCLOPROPANECARBOXAMIDO)-4-((2-METHOXY-3-(1-METHYL-1H-1,2,4-TRIAZOL-3-YL)PHENYL)AMINO)-N-(METHYL-D3) PYRIDAZINE-3-CARBOXAMIDE

(71) Applicant: BRISTOL-MYERS SQUIBB COMPANY, Princeton, NJ (US)

(72) Inventor: Daniel Richard Roberts, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 92 days.

(21) Appl. No.: 17/058,698

(22) PCT Filed: May 30, 2019

(86) PCT No.: PCT/US2019/034534
§ 371 (c)(1),
(2) Date: Nov. 25, 2020

(87) PCT Pub. No.: WO2019/232138
PCT Pub. Date: Dec. 5, 2019

(65) Prior Publication Data
US 2021/0206748 A1    Jul. 8, 2021

Related U.S. Application Data

(60) Provisional application No. 62/678,451, filed on May 31, 2018.

(51) Int. Cl.
*C07D 403/12* (2006.01)

(52) U.S. Cl.
CPC ........ *C07D 403/12* (2013.01); *C07B 2200/05* (2013.01); *C07B 2200/13* (2013.01)

(58) Field of Classification Search
CPC .......................... C07D 403/12; C07B 2200/13
See application file for complete search history.

(56) References Cited

U.S. PATENT DOCUMENTS 9,505,748 B2    11/2016    Moslin et al.

OTHER PUBLICATIONS

Caira M.R. (1998) Crystalline Polymorphism of Organic Compounds. In: Weber E. et al. (eds) Design of Organic Solids. Topics in Current Chemistry, vol. 198. Springer, Berlin, Heidelberg.

*Primary Examiner* — Sikarl A Witherspoon
(74) *Attorney, Agent, or Firm* — Covington & Burling LLP; Jennifer L. Robbins; Melody Wu

(57) ABSTRACT

Disclosed is crystalline Form B of 6-(cyclopropanecarboxamido)-4-((2-methoxy-3-(1-methy-1H-1,2,4-triazol-3-yl) phenyl) amino)-N-methyl-d3)pyridazine-3-carboxamide. Form B is the HCl salt of a neat crystalline form. Characterization data for Form B are disclosed.

32 Claims, 5 Drawing Sheets

CRYSTALLINE FORM OF 6-(CYCLOPROPANECARBOXAMIDO)-4-((2-METHOXY-3-(1-METHYL-1H-1,2,4-TRIAZOL-3-YL)PHENYL)AMINO)-N-(METHYL-D3) PYRIDAZINE-3-CARBOXAMIDE

CROSS-REFERENCE TO RELATED APPLICATIONS

This application claims the benefit of U.S. Provisional Application No. 62/678,451, filed May 31, 2018, the disclosure of which is incorporated herein by reference in its entirety.

FIELD OF THE INVENTION

The present invention generally relates to a crystalline form of 6-(cyclopropanecarboxamido)-4-((2-methoxy-3-(1-methyl-1H-1,2,4-triazol-3-yl)phenyl) amino)-N-(methyl-$d_3$) pyridazine-3-carboxamide HCl salt, hereinafter referred to as "Form B".

BACKGROUND OF THE INVENTION

The compound, 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide, has the structure of Formula (I):

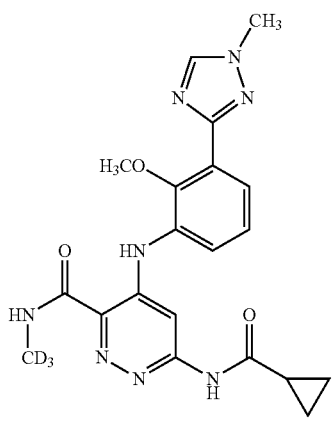

(I)

and is referred to herein as "Compound (I)". Compound (I) is disclosed U.S. Pat. No. 9,505,748 B2, which is assigned to the present assignee. U.S. Pat. No. 9,505,748 B2 also discloses methods of treatment employing Compound (I).

Compound (I) is a Tyk2 inhibitor currently in clinical trials for the treatment of auto-immune and auto-inflammatory diseases such as psoriasis, psoriatic arthritis, lupus, lupus nephritis, Sjögren's syndrome, inflammatory bowel disease, Crohn's disease and ankylosing spondylitis.

In the synthesis of a chemical compound intended for pharmaceutical use, it is necessary to isolate and purify the compound at the completion of the synthetic process and prior to further processing to provide the compound in a pharmaceutical formulation. The isolation and the purification steps, which can be combined or separate consecutive steps, provide the compound as a purified solid with minimal loss of yield during isolation from other components of the reaction mixture and/or during purification to remove impurities from the isolated compound sample.

It is desirable to provide a solid form that can be reproducibly produced from the isolation and/or purification steps.

Further, it is desirable to isolate the purified compound in a solid form that is physically and chemically stable at a range of storage conditions, such as at different conditions of temperature and humidity.

Furthermore, it is also desirable to provide the compound in a solid form that is amenable to additional processing, for example, in which it can be converted into other solids forms, such as an amorphous form.

Still furthermore, it is desirable to provide a compound in a solid form that has sufficient solubility in solvents/solutions to permit preparation of other solid forms.

The Applicants have found a crystalline form of Compound (I) that surprisingly provides Compound (I) in a solid form that is physically and chemically stable at a range of storage conditions.

Further, the Applicants have found a crystalline form of Compound (I) that surprisingly provides Compound (I) in a solid form that is physically and chemically stable at a range of storage conditions, and has sufficient solubility in solvents/solutions to permit preparation of other solid forms.

Further, the Applicants have found a crystalline form of Compound (I) that surprisingly provides Compound (I) in a solid form that mitigates pH effects better than other salts tested.

The present invention is also directed to other important aspects.

SUMMARY OF THE INVENTION

The present invention provides crystalline Form B of Compound (I). The name used herein to characterize a specific form, e.g. "Form B" etc., should not be considered limiting with respect to any other substance possessing similar or identical physical and chemical characteristics, but rather it should be understood that this designation is a mere identifier that should be interpreted according to the characterization information also presented herein.

DETAILED DESCRIPTION OF THE INVENTION

Figure 1:
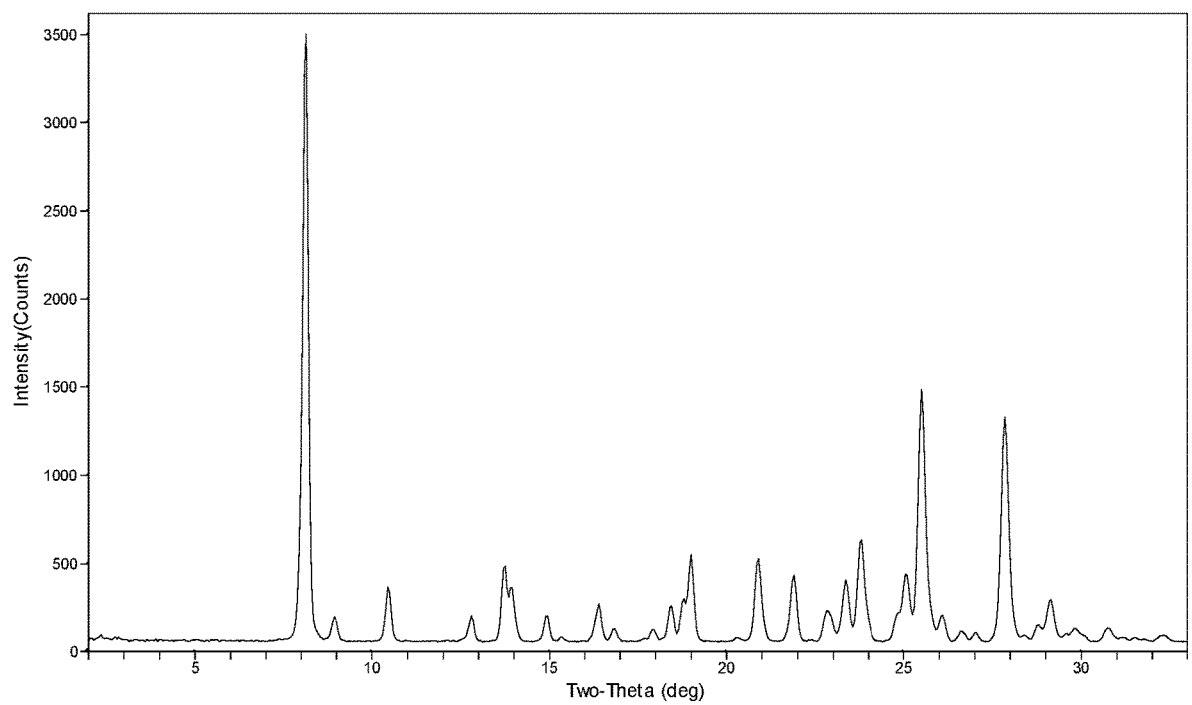
FIG. 1. shows the observed powder x-ray diffraction pattern (CuKα, at T=25° C.) of crystalline Form B of Compound (I).

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g., "Form B" etc., are merely identifiers that are to be interpreted in accordance with the characterization information presented herein and are not to be limited so as to exclude any other substance possessing similar or identical physical and chemical characteristics.

The definitions set forth herein take precedence over definitions set forth in any patent, patent application, and/or patent application publication incorporated herein by reference.

All numbers expressing quantities of ingredients, weight percentages (wt %), temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

As used herein, "polymorphs" refer to crystalline forms having the same chemical structure but different spatial arrangements of the molecules and/or ions forming the crystals.

As used herein, "amorphous" refers to a solid form of a molecule and/or ion that is not crystalline. An amorphous solid does not display a definitive X-ray diffraction pattern with sharp maxima.

As used herein, "substantially pure," when used in reference to a crystalline form, means a compound having a purity greater than 90 weight %, including greater than 90, 91, 92, 93, 94, 95, 96, 97, 98, and 99 weight %, and also including equal to about 100 weight % of Compound (I), based on the weight of the compound. The remaining material comprises other form(s) of the compound, and/or reaction impurities and/or processing impurities arising from its preparation. For example, a crystalline form of Compound (I) may be deemed substantially pure in that it has a purity greater than 90 weight %, as measured by means that are at this time known and generally accepted in the art, where the remaining less than 10 weight % of material comprises amorphous and/or other form(s) of Compound (I) and/or reaction impurities and/or processing impurities.

As used herein, a powder x-ray diffraction (PXRD) pattern "comprising" a number of peaks selected from a specified group of peaks, is intended to include PXRD patterns having additional peaks that are not included in the specified group of peaks. For example, a PXRD pattern comprising four or more, preferably five or more, 2θ values selected from: A, B, C, D, E, F, G, and H is intended to include a PXRD pattern having: (a) four or more, preferably five or more, 2θ values selected from: A, B, C, D, E, F, G, and H; and (b) zero or more peaks that are not one of peaks A, B, C, D, E, F, G, and H.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the unit cell parameter "molecules per unit cell" refers to the number of molecules of Compound (I) in the unit cell.

Form B of Example (I)

In one embodiment, Compound (I) is provided as a crystalline material comprising Form B. The crystalline Form B of Compound (I) is a HCl salt.

In one embodiment, crystalline Form B of Compound (I) is characterized by unit cell parameters approximately equal to the following:

a=8.55±0.05 Å
b=11.60±0.05 Å
c=12.00±0.05 Å
α=114.3±0.5°
β=94.1±0.5°
γ=93.31±0.5°
Space group: P-1
Molecules per unit cell (Z): 2
Unit cell volume=1077±10 Å$^3$
Calculated density 1.424 g/cm$^3$ wherein the unit cell parameters of Form B of Compound (I) are measured at a temperature of about 25° C.

TABLE 1

Form B of Compound (I)
Selected PXRD 2θ values in degrees (CuKα)

| | | | | | | |
|---|---|---|---|---|---|---|
| 8.1 ± 0.2 | 8.9 ± 0.2 | 10.4 ± 0.2 | 12.8 ± 0.2 | 14.9 ± 0.2 | 16.4 ± 0.2 | 16.8 ± 0.2 |
| 17.9 ± 0.2 | 18.4 ± 0.2 | 20.8 ± 0.2 | 21.8 ± 0.2 | 22.8 ± 0.2 | 23.3 ± 0.2 | 23.8 ± 0.2 |
| 24.8 ± 0.2 | 25.1 ± 0.2 | 25.4 ± 0.2 | 26.1 ± 0.2 | 26.6 ± 0.2 | 27.0 ± 0.2 | 27.8 ± 0.2 |
| 28.4 ± 0.2 | 28.8 ± 0.2 | 29.1 ± 0.2 | 29.6 ± 0.2 | 29.9 ± 0.2 | 30.7 ± 0.2 | |

TABLE 2

| $^{13}$C ssNMR chemical shift values of Form B of Compound (I) ppm (±0.2) |
|---|
| 175.0 |
| 167.6 |
| 156.3 |
| 150.9 |
| 147.2 |
| 144.4 |
| 142.7 |
| 138.2 |
| 136.3 |
| 125.0 |
| 121.6 |
| 117.5 |
| 98.3 |
| 59.8 |
| 40.6 |
| 26.9 |
| 15.6 |
| 10.3 |
| 7.2 |

In one embodiment, crystalline Form B of Compound (I) is characterized by a powder x-ray diffraction pattern comprising four or more 2θ values in degrees (CuKα) selected from: 8.1±0.2; 8.9±0.2; 10.4±0.2; 12.8±0.2; 14.9±0.2; 16.4±0.2; and 18.4±0.2, wherein the PXRD pattern of Form B is measured at a temperature of about 25° C.

In one embodiment, crystalline Form B of Compound (I) is characterized by a powder x-ray diffraction pattern comprising five or more 2θ values in degrees (CuKα) selected from: 8.1±0.2; 8.9±0.2; 10.4±0.2; 12.8±0.2; 14.9±0.2; 16.4±0.2; and 18.4±0.2, wherein the PXRD pattern of Form B is measured at a temperature of about 25° C.

In one embodiment, crystalline Form B of Compound (I) is characterized by a powder x-ray diffraction pattern comprising six or more 2θ values in degrees (CuKα) selected from: 8.1±0.2; 8.9±0.2; 10.4±0.2; 12.8±0.2; 14.9±0.2; 16.4±0.2; and 18.4±0.2, wherein the PXRD pattern of Form B is measured at a temperature of about 25° C.

In one embodiment, crystalline Form B of Compound (I) is characterized by a powder x-ray diffraction pattern comprising 2θ values in degrees (CuKα) at 8.1±0.2 and 12.8±0.2; and three or more 2θ values in degrees (CuKα) selected from: 8.9±0.2; 10.4±0.2; 14.9±0.2; 16.4±0.2 and 18.4±0.2; wherein the PXRD pattern of Form B is measured at a temperature of about 25° C.

In one embodiment, crystalline Form B of Compound (I) is characterized by a $^{13}C$ ssNMR spectrum comprising four or more chemical shift values in ppm (all ±0.2) selected from: 175.0; 167.6; 156.3; 150.9; 147.2; 144.4; 142.7; 138.2; 136.3; 125.0; 121.6; 117.5; 98.3; 59.8; 40.6; 26.9; 15.6; 10.3 and 7.2; wherein the spectrum of Form B is measured at a temperature of about 280° K.

In one embodiment, crystalline Form B of Compound (I) is characterized by a $^{13}C$ ssNMR spectrum comprising five or more chemical shift values in ppm (all ±0.2) selected from: 175.0; 167.6; 156.3; 150.9; 147.2; 144.4; 142.7; 138.2; 136.3; 125.0; 121.6; 117.5; 98.3; 59.8; 40.6; 26.9; 15.6; 10.3 and 7.2; wherein the spectrum of Form B is measured at a temperature of about 280° K.

In one embodiment, crystalline Form B of Compound (I) is characterized by a $^{13}C$ ssNMR spectrum comprising six or more chemical shift values in ppm (all ±0.2) selected from: 175.0; 167.6; 156.3; 150.9;147.2; 144.4; 142.7; 138.2; 136.3; 125.0121.6; 117.5; 98.3; 59.8; 40.6; 26.9; 15.6; 10.3 and 7.2; wherein the spectrum of Form B is measured at a temperature of about 280° K.

In one embodiment, crystalline Form B of Compound (I) is characterized by a $^{13}C$ ssNMR spectrum comprising chemical shift values in ppm (all ±0.2) at 117.5 and 40.6; and three or more chemical shift values in ppm selected from: 175.0; 167.6; 156.3; 150.9; 147.2; 144.4; 142.7; 138.2; 136.3; 125.0; 121.6; 98.3; 59.8; 26.9; 15.6; 10.3 and 7.2; wherein the spectrum of Form B is measured at a temperature of about 280° K.

In one embodiment, crystalline Form B of Compound (I) is characterized by (i) a powder x-ray diffraction pattern comprising the 2θ values in degrees (CuKα) at 8.1±0.2 and 12.8±0.2, measured at a temperature of about 25° C.; and (ii) a broad endotherm in the approximate range of from about 203° C. to about 217° C.

In one embodiment, crystalline Form B of Compound (I) is characterized by an observed powder x-ray diffraction pattern substantially as shown in FIG. 1.

In one embodiment, crystalline Form B of Compound (I) is characterized by a broad endotherm in the approximate range of from about 203° C. to about 217° C.

Figure 2:
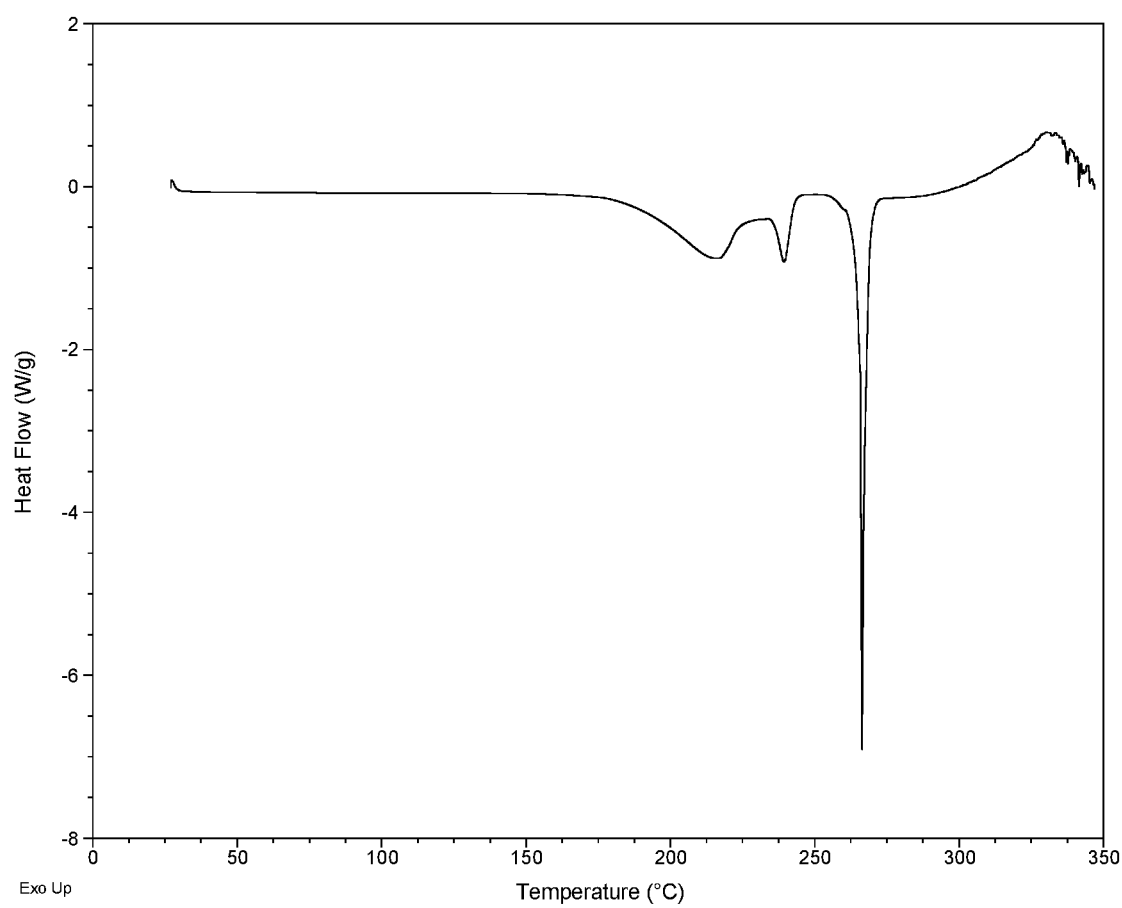
FIG. 2 shows a differential scanning calorimetry (DSC) thermogram of crystalline Form B of Compound (I).

In one embodiment, crystalline Form B of Compound (I) is characterized by a differential scanning calorimetry (DSC) thermogram substantially as shown in FIG. 2.

In one embodiment, crystalline Form B of Compound (I) is characterized by (i) a powder x-ray diffraction pattern comprising the 2θ values in degrees (CuKα) at 8.1±0.2 and 12.8±0.2, measured at a temperature of about 25° C.; and (ii) a differential scanning calorimetry (DSC) thermogram substantially in accordance with that shown in FIG. 2.

In one embodiment, crystalline Form B of Compound (I) is characterized by a thermogravimetric analysis (TGA) thermogram having weight loss of less than 0.2%, based on the weight of the sample of Form B, upon being heated to a temperature of about 150° C.

Figure 3:
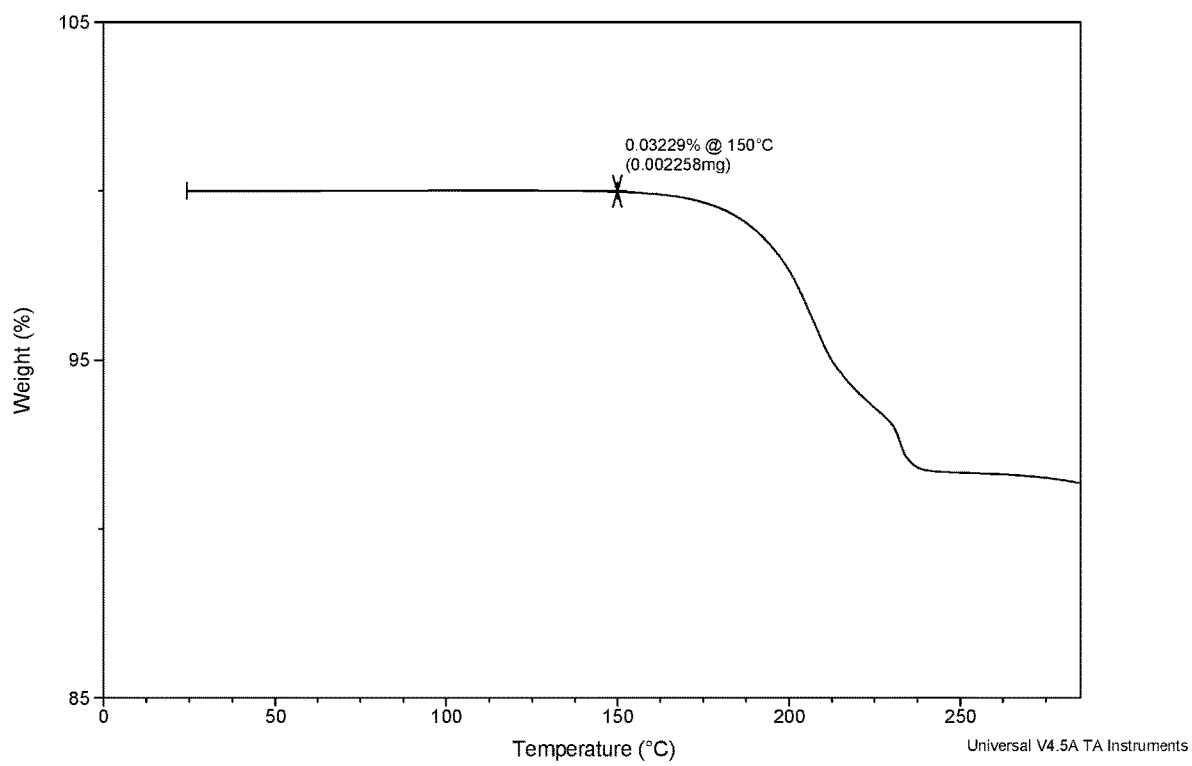
FIG. 3 shows a thermogravimetric analysis (TGA) thermogram of Form B of Compound (I).

In one embodiment, crystalline Form B of Compound (I) exhibits a thermogravimetric analysis (TGA) thermogram substantially as shown in FIG. 3.

Figure 4:
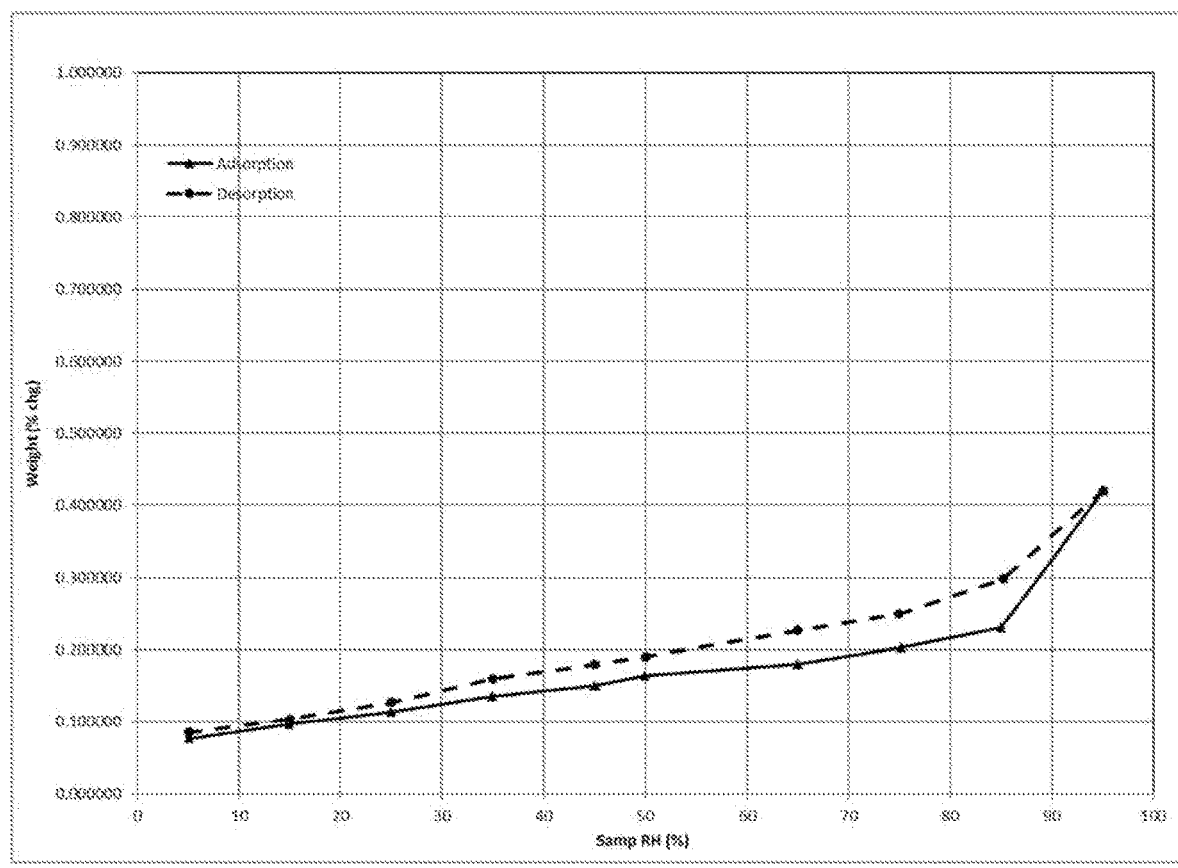
FIG. 4 shows a moisture-sorption isotherms for Form B of Compound (I) measured at 25° C.

In one embodiment, crystalline Form B of Compound (I) exhibits a moisture-sorption isotherms substantially as shown in FIG. 4.

Figure 5:
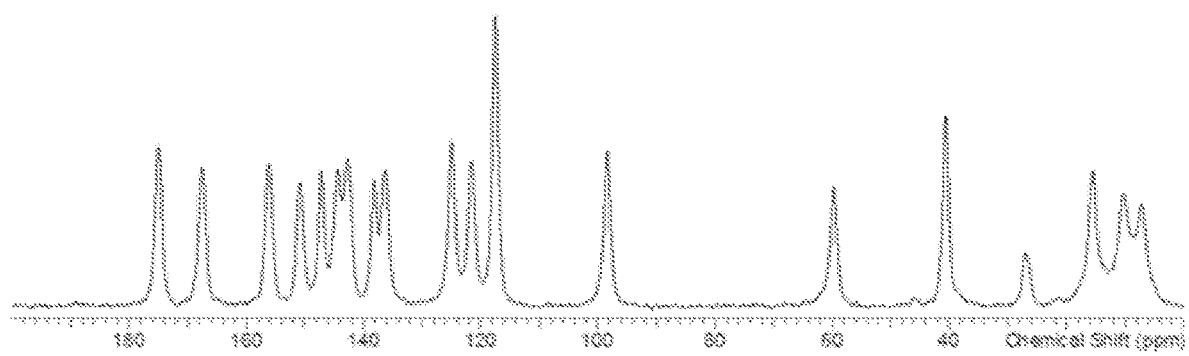
FIG. 5 shows the $^{13}$C solid-state nuclear magnetic resonance (ssNMR) spectrum of Form B of Compound (I).

In one embodiment, crystalline Form B of Compound (I) is characterized by a solid-state NMR (ssNMR) substantially as shown in FIG. 5.

In still yet an even further embodiment, crystalline Form B of Compound (I) is substantially pure.

In another embodiment, the crystalline form of Compound (I) consists essentially of Form B. The crystalline form of this embodiment may comprise at least about 90 wt %, preferably at least about 95 wt %, and more preferably at least about 99 wt %, based on the weight of the crystalline form, Form B of Compound (I).

One embodiment provides a composition comprising 6-(cyclopropane carboxamido)-4-((2-methoxy-3-(1-methyl-1H-1,2,4-triazol-3-yl)phenyl) amino)-N-(methyl-d$_3$) pyridazine-3-carboxamide, wherein at least 95 wt %, preferably at least 97 wt %, and more preferably at least 99 wt % of said 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide is in crystalline Form B.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Bym, R. R. Pfeiffer, and J. G. Stowell, 2$^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described for example, in "Programmed Cooling of Batch Crystallizers," J. W. Mullin and J. Nyvlt, *Chemical Engineering Science,* 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form from the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid-state nuclear magnetic resonance, differential scanning calorimetry, powder x-ray diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Crystalline forms may be prepared directly from the reaction medium of the final process for preparing Compound (I). This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one polymorph in a sample may be determined by techniques such as powder x-ray diffraction (PXRD) or solid-state nuclear magnetic resonance (ssNMR) spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data, see Smith, D. K., "*A FORTRAN Program for Calculating X-Ray Powder Diffraction Patterns*." Lawrence Radiation Laboratory, Livermore, Calif., UCRL-7196 (April 1963).

Form B of Compound (I) may be characterized using various techniques, the operation of which are well known to those of ordinary skill in the art. The forms may be characterized and distinguished using single crystal x-ray diffraction, which is based on unit cell measurements of a single crystal at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, another means of characterizing the crystalline structure is by powder x-ray diffraction analysis in which the diffraction profile is compared to a simulated profile representing pure powder material, both run at the same analytical temperature, and measurements for the subject form characterized as a series of $2\theta$ values in degrees (usually four or more).

Other means of characterizing the form may be used, such as solid-state nuclear magnetic resonance, differential scanning calorimetry, thermal analysis, and vibrational spectroscopy. These parameters may also be used in combination to characterize the subject form.

UTILITY

Crystalline Form B of Compound (I) can be used to isolate Compound (I) from other components at the completion of the synthesis process; and/or to purify Compound (I) by one or a series of crystallization steps. The isolation and the purification steps can be combined or practiced as separate process steps.

EXAMPLE

The invention will now be further described by the following working example(s) which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

For ease of reference, the following abbreviations may be used herein.

| Abbreviations | |
|---|---|
| Abbreviation | Name |
| ACN or MeCN | Acetonitrile |
| AcOH | acetic acid |
| AP | area percent |
| aq. | Aqueous |
| BuOAc | butyl acetate |
| conc. | Concentrated |
| DBU | 1,8-diazabicyclo[5.4.0]undec-7-ene |
| DCM | Dichloromethane |
| DIPEA | N,N-diisopropylethylamine (Hunig's base) |
| DMA | Dimethylacetamide |
| EDC HCl | 1-(dimethylaminopropyl)-3-ethylcarbodiimide hydrochloride |
| equiv. | molar equivalents |
| Et | Ethyl |
| EtOAc | ethyl acetate |
| h | hour(s) |
| HIL | High intensity light |
| HOBt | 1-hydroxy benzotriazole |
| HPLC | high pressure liquid chromatography |
| IPA | isopropyl alcohol |
| min | minute(s) |
| Me | Methyl |
| mL | Millimeter |
| NaOH | sodium hydroxide |
| MTBE | methyl tert-butyl ether |
| NMI | N-methyl-imidazole |
| NMP | n-methylpyrrolidone |

-continued

Abbreviations

| Abbreviation | Name |
| --- | --- |
| NMR | nuclear magnetic resonance |
| $Pd_2(dba)_3$ | tris-(dibenzylideneacetone)dipalladium |
| Pd/C | palladium on carbon |
| ppm | Parts per million |
| RH | Relative humidity |
| rt/RT | room temperature |
| sat. | saturated |
| t-BuOK | potassium tert-butoxide |
| TEA | triethanolamine |
| THF | tetrahydrofuran |
| TsCl | p-toluenesulfonyl chloride |
| XANTPHOS | 4,5-bis(diphenylphosphino)-9,9 dimethylxanthene |
| 2-Me THF | 2-methyl tetrahydrofuran |

Example 1: Preparation of Crystalline Form B of Compound (I)

A solution was prepared by mixing 51 mg of Compound (I) and 0.5 mL of 0.25 M HCl into 2 mL of IPA and heating to 55° C. The mixture was stirred overnight at 55° C., after which the heat was turned off and left to stir overnight at room temperature resulting in a thick slurry of Form B of Compound (I).

Example 2: Preparation of Crystalline Form B of Compound (I)

A solution was prepared by mixing 550 mg of Compound (I) into 35 mL THF and 2 mL water at room temperature (25° C.) until fully solubilized into which 108 µL, of 37% HCl were added. The resulting slurry was dried overnight using a Speedvac. The dried solid was suspended in 5 mL of BuOAc at 60° C. and the resulting slurry was aged at 60° C. overnight. The slurry was filtered and the wet cake was dried in a vacuum oven at a temperature in the range of 50-60° C. to afford Compound (I) Form B.

Example 3: Preparation of Crystalline Form B of Compound (I)

A HCl solution was prepared by mixing 395 µL of 37% HCl (1.0 molar equivalent), 25 mL of BuOAc, and 7.6 mL of DMA at 60° C. Separately, 2 g of Compound I and 15 mL of DMA were charged into a 100 mL three-neck round bottom flask at 60° C. resulting in a clear solution, into which 3 mL of the HCl solution is added maintaining the clear solution. A cloudy solution was generated after adding 40 mg of Compound (I) Form B seeds after which the remaining HCl solution was added to over 3 hours with a syringe pump. The resulting slurry was cooled from 60° C. to 50° C. over one hour and left to stir at 50° C. for 15 hours. The slurry was then cooled to 20° C. over one hour and left to stir overnight. The cooled slurry was then filtered and the wet cake was washed with 6 mL of BuOAc. The wet cake was dried in a vacuum oven overnight at 50° C. affording 2.1 g of Compound (I) HCl salt Form B (93% yield).

Example 4: Preparation of Crystalline Form B of Compound (I)

A solution was prepared by charging 1.4 kg of Compound (I) CRUDE and 8.400 L of NMP and heating to 50° C. The resulting solution was polish filtered over a bed of Celite 545 at 50° C. The dissolution vessel was rinsed twice with 2.5 L of NMP and each rinse was also polish filtered. The solution was heated to 50° C. and 0.421 kg of hydrochloric acid 37 wt % solution to form Compound (I) HCl salt in solution. 14 L of ethyl acetate were charged to the batch over 30 minutes to Form B slurry. The slurry was cooled to 20° C. over 60 minutes. The cooled slurry was aged for 12 hours, after which it was filtered. The wet cake was washed with 2×5.6 L of ethyl acetate. The wet cake was put into a vacuum oven and dried at 55° C. to afford 1.3 kg of Compound (I) (98.95 AP, 85.2% yield) in Form B.

Example 5: Preparation of Crystalline Form B of Compound (I)

A solution was prepared by charging 2.323 kg of Compound (I) CRUDE and 16.26 L of NMP and heating to 50° C. The resulting solution was polish filtered at 50° C. The dissolution vessel was rinsed 2.32 L of NMP and the rinse was also polish filtered. The solution was heated to 50° C. and 0.55 kg of hydrochloric acid 37 wt % solution to form Compound (I) HCl salt in solution. 0.04 kg of Compound (I) Form B seeds and 0.47 L of ethyl acetate were charged to the batch to generate a slurry. The resulting slurry was aged for 90 minutes and then 13.48 L of ethyl acetate was charged to the batch over 60 minutes. The slurry was aged at 50° C. for 60 minutes and then the slurry cooled to 20° C. over 60 minutes. The cooled slurry was aged for 12 hours, after which it was filtered. The wet cake was washed with 2×9.29 L of ethyl acetate. The wet cake was put into a vacuum oven and dried at 65° C. to afford 2.27 kg of Compound (1) (99.93 AP, 89.1% yield) in Form B.

Synthesis of 6-(cyclopropanecarboxamido)-4-((2-methoxy-3-(1-methyl-1H-1,2,4-triazol-3-yl)phenyl)amino)-N-(methyl-d$_3$)pyridazine-3-carboxamide Step 1: Preparation of Compound 2

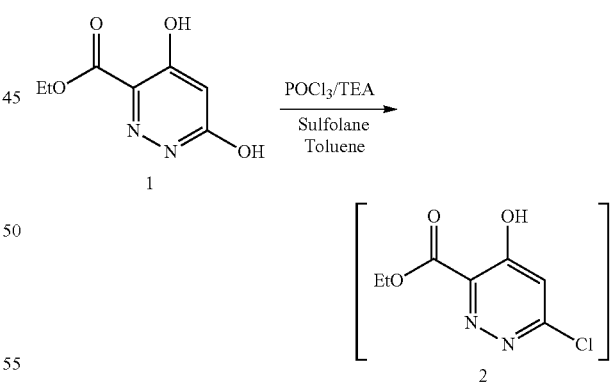

To a glass lined reactor were charged toluene (0.26 kg), sulfolane (3.4 kg), Compound 1 (1.0 kg) and POCl$_3$ (2.7 kg). The crude was cooled to 0° C. Triethylamine (0.89 kg) was charged, and the resulting crude mixture was heated to 65° C. and aged till the reaction reached completion. The reaction mass was cooled to 5° C.

In a separate reactor, water (7.5 kg) was charged and cooled to 5° C. The reaction mass was added slowly to the water solution, maintaining the internal temperature below 5° C. Additional water (0.5 kg) was used to rinse the reactor and aid the transfer. The resulting mixture was agitated at 5° C. for 3 hours, then extracted with MTBE three times (3×4.5 kg). The combined organic layers were washed sequentially with aqueous pH 7 buffer solution (5.0 L/kg, 15 wt % KH$_2$PO$_4$/K$_2$HPO$_4$) and water (2.5 kg). The crude was distilled under vacuum until total volume became approximately 3 L/kg. ACN (2×6.3 kg) was added followed by additional distillations back to ~3 L/kg. The crude was cooled to 20° C. to afford Compound 2 as a 30-36 wt % solution in 90-95% yield.

Step 2: Preparation of Compound 3

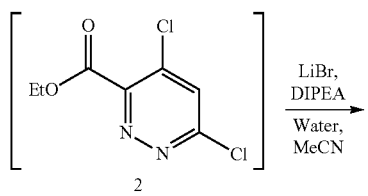

ACN (2.7 kg), lithium bromide (1.18 kg) and water (0.65 kg) were charged to a glass-lined reactor at 25° C. Compound 2 crude solution prepared above (limiting reagent) was added, followed by DIPEA (1.82 kg). The resulting slurry was agitated at 25° C. until the reaction reached completion. The product was isolated by filtration. The crude solid was washed with ACN (1.6 kg). The cake was dried under vacuum at 45° C. Compound 3 was isolated in 98 AP and 83% yield.

Step 3: Preparation of Compound 8

Water (6.0 kg, 6.0 L/kg) and Compound 7 (1.0 kg) were charged to a glass-lined reactor at 25° C. Zinc acetate dehydrate (1.08 kg, 1.0 equiv.) was added, followed by Compound 3 (1.28 kg, 1.20 equiv.). The reactor line was rinsed with 2-propanol (0.79 kg, 1.0 L/kg) and water (1.50 kg, 1.50 L/kg). The resulting homogeneous solution was heated to 65° C. and aged until the reaction reached completion. Water (7.0 kg, 7.0 L/kg) was added, and the crude mixture was cooled to 20° C. and aged for 30 min. The product was isolated by filtration. The crude solid was washed sequentially with water (6.0 kg, 2θ 6.0 L/kg), water (6.0 kg, 6.0 L/kg), THF (5.3 kg, 6.0 L/kg) and THF (5.3 kg, 6.0 L/kg). The cake was dried under vacuum at 70° C. Compound 8 was isolated in 98 AP and 94% yield.

Step 4: Preparation of Compound 9

Step 5: Preparation of the Compound (I)

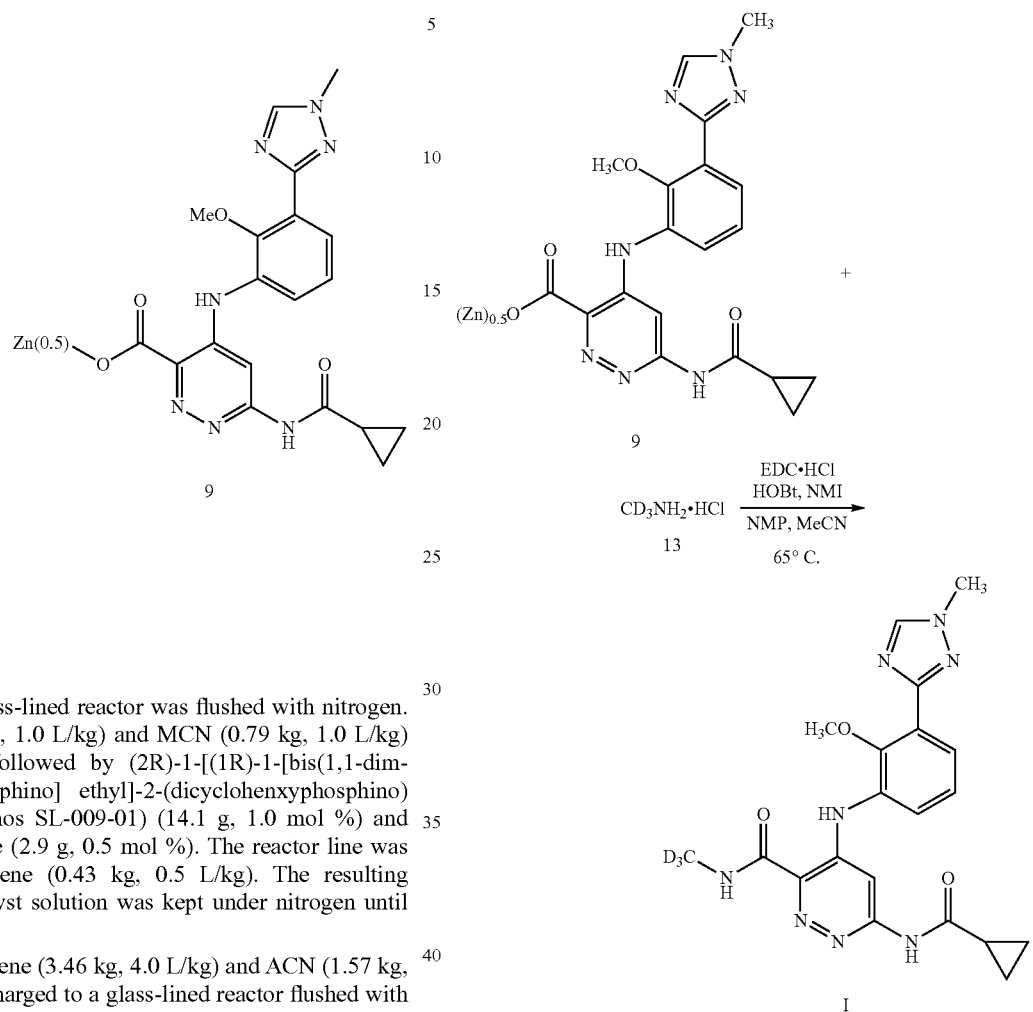

A separate glass-lined reactor was flushed with nitrogen. Toluene (0.87 kg, 1.0 L/kg) and MCN (0.79 kg, 1.0 L/kg) were charged, followed by (2R)-1-[(1R)-1-[bis(1,1-dimethylethyl) phosphino] ethyl]-2-(dicyclohenxyphosphino) ferrocene (Josiphos SL-009-01) (14.1 g, 1.0 mol %) and palladium acetate (2.9 g, 0.5 mol %). The reactor line was rinsed with toluene (0.43 kg, 0.5 L/kg). The resulting pre-formed catalyst solution was kept under nitrogen until further usage.

At 20° C., toluene (3.46 kg, 4.0 L/kg) and ACN (1.57 kg, 2.0 L/kg) were charged to a glass-lined reactor flushed with nitrogen. Compound 8 (1.00 kg) was added, followed by DBU (0.39 kg, 1.00 equiv). The reactor line was rinsed with toluene (0.43 kg, 0.5 L/kg). Compound 10 (0.54 kg, 2.5 equiv) and $K_2CO_3$ (325 mesh grade, 0.70 kg, 2.0 equiv) were added to the reaction mixture, followed by toluene (1.30 kg, 1.5 L/kg) and ACN (0.79 kg, 1.0 L/kg). The pre-formed catalyst solution was transferred into the reaction mixture, which was then heated to 75° C. and agitated until the reaction reached completion.

The reaction crude was cooled to 20° C. Aqueous acetic acid (50 Volume %, 4.0 kg, 4.0 L/kg) was charged slowly over the course of 1 h. Glacial acetic acid (10.5 kg, 10.0 L/kg) was then added. The resulting homogeneous solution was washed twice with heptane (2×3.42 kg, 2×5.0 L/kg). The bottom aqueous layer was collected and transferred to a clean reactor. Water (5.0 kg, 5.0 L/kg) was added, followed by Compound 9 seeds (0.01 kg, 1.0 wt %). The slurry was aged for 2 h at 20° C. Additional water (2.0 kg, 2.0 L/kg) was added, and the slurry was further aged for 6 h. The product was isolated by filtration. The crude cake was washed with aqueous ACN (50 Volume %, 4.5 kg, 5.0 L/kg) followed by ACN (3.9 kg, 5.0 L/kg). The cake was dried under vacuum at 65° C. Compound 9 was isolated in 98.5 AP and 84% yield.

NMP (2.06 kg, 2.0 L/kg) and ACN (0.78 kg, 1.0 L/kg) were charged to a glass-lined reactor and agitated at 20° C. N-Methylimidazole (0.13 kg, 0.7 equiv.), Compound 13 (0.17 kg, 1.2 equiv.) and Compound 9 (1.00 kg) were charged to the reaction mixture. The mixture was heated to 65° C. and aged until homogeneous. HOBt 20% wet (0.17 kg, 0.5 eq), followed by EDC HCl (0.54 kg, 1.4 eq) were then charged to the reaction mixture. The reactor was rinsed with ACN (0.78 kg, 1.0 L/kg), then the resulting mixture was aged at 65° C. until the reaction reached completion. The reaction was quenched by charging water (1.0 kg, 1 L/kg), then diluted with ACN (3.0 kg, 3 L/kg). The reaction mixture was aged at 65° C. for 1 h, before cooling to 0° C., and aged for an additional 12 h at 0° C. The product was isolated by filtration. The wet cake was washed with 2:1 Water:ACN (2.8 kg, 3 L/kg) then ACN (2.4 kg, 3 L/kg), before drying under full vacuum at 65° C. Compound (I) was isolated in >99.5% purity and 91% yield.

NMP (6.2 kg, 6.0 L/kg) and Compound (I) (1.0 kg) were charged to a glass-lined reactor. The batch was heated to 70° C. to form a pale yellow solution, which was then transferred through a polish filter to a clean vessel at 70° C. 2-Propanol (2.4 kg, 3 L/kg) was added, followed by Compound (I) seeds (0.005 kg, 0.005 kg/kg). After aging for 1 h, additional 2-propanol (4.8 kg, 6 L/kg) was charged over the course of 2 h (3 L/kg/h). The slurry was aged for 1 h at 70° C. cooled slowly to 0° C. and aged for additional 12 h at 0° C. Product was isolated by filtration. The wet cake was washed with 2-propanol (2×3.1 kg, 2×4 L/kg) before drying under full vacuum at 65° C. Compound (I) was isolated in >99.9% purity and 83% yield.

Preparation of Compound 7

Step 1: Preparation of N-methyl-N-formyl hydrazine

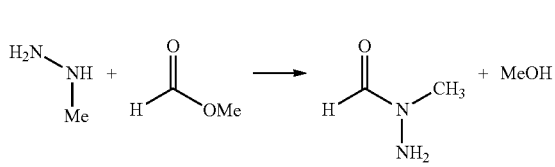

To a glass lined reactor were charged methanol (1.6 kg/kg, 2.0 L/kg) and methyl hydrazine (1 kg) at 0° C. Methyl formate (0.57 kg/kg, 1.1 equiv) was added drop-wise. The crude was warmed up to 20° C. and aged for additional 6 h. The crude was distilled under vacuum until total volume became approximately 0.5 L/kg. Five put/take distillations with 2-MeTHF (5×3.6 kg/kg) were undertaken for azeotropic drying. The crude was cooled to 20° C. N-Methyl-N-formyl hydrazine was isolated as 89-90 wt % solution in 89-91% yield.

Step 2: Preparation of Compound 5

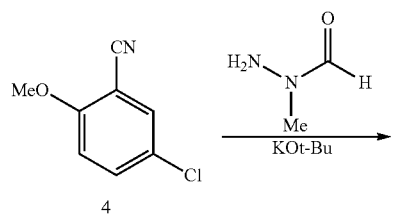

To a glass lined reactor were charged potassium tert-butoxide (1.5 kg/kg, 2.4 equiv) and THF (12.2 kg/kg) at 0° C. A mixture of Compound 4 (1.0 kg), N-methyl-N-formyl hydrazine (1.0 kg/kg, 2.30 equiv) and THF (5.3 kg/kg, 6.0 L/kg) was added slowly. The reactor line was rinsed with THF (0.5 kg/kg). The reaction crude was aged at 0° C. until reaction reached completion. Water (5.0 kg/kg) was added, and the resulting mixture was aged at 0° C. for 30 min, heated to 40° C. and aged for additional 30 min. The layers were separated and the aqueous layer was discarded. The organic layer was washed with brine (15 wt %. 5.7 kg/kg) before distilling under vacuum until total volume became approximately 5 L/kg. Four put/take distillations with ethyl acetate (4×10 L/kg) were undertaken for the purpose of azeotropic drying. The crude was cooled to 20° C. Sulfuric acid (0.66 kg/kg. 1.10 equiv.) was added, and the slurry was agitated for 2-3 h. Product was isolated by filtration. The cake was consecutively washed with ethyl acetate (2×6.5 L/kg) and heptane (8 L/kg), and dried under vacuum at 45° C. Compound 5 was isolated in 99 AP and 83% yield.

Step 3: Preparation of Compound 6

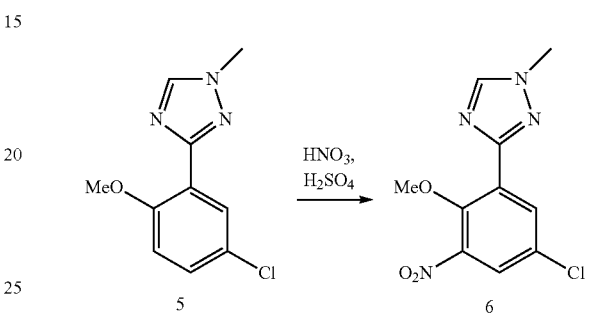

To a glass lined reactor were charged concentrated sulfuric acid (4.5 kg/kg) and Compound 5 (1.0 kg) at 0-5° C. Nitric acid (68 wt %, 0.35 kg/kg, 1.2 equiv.) was added drop-wise. The mixture was agitated at 0-5° C. until reaction reached completion.

In a separate reactor, water (12 kg/kg) and methanol (6.5 kg/kg. 8.3 L/kg) were mixed well at 20° C. The nitration crude was transferred slowly into the methanol water mixture. The reactor line was rinsed with methanol (0.5 kg/kg). The crude was heated to 40-45° C. Aqueous ammonium hydroxide (25 wt %, 7.4 kg/kg) was added slowly. The resulting slurry was cooled to 20° C. and agitated for 3 h. Product was isolated by filtration. The cake was washed with water (2×6 L/kg), and dried under vacuum at 45° C. Compound 6 was isolated in 99 AP and 95% yield.

Step 4: Preparation of Compound 7

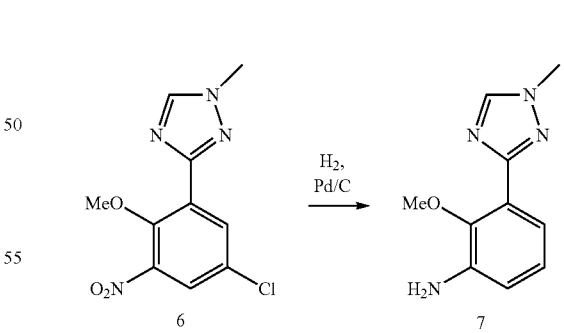

To a high pressure reactor flushed with nitrogen were charged methanol (8.0 kg/kg) and Compound 6 (1.0 kg). With careful exclusion of oxygen, sodium bicarbonate (0.6 kg/kg, 2.0 equiv.) and Pd/C (10% loading, 50% wet, 0.02 kg/kg) were added. The reactor was pressurized with hydrogen (41-46 psi), and the reaction mixture was aged at 20° C. for 6 h then heated to 45° C. and aged till reaction reached completion. The reactor was flushed with nitrogen, and the reaction crude was filtered to remove Pd/C. Methanol (5 kg/kg) was used to aid the transfer. The combined filtrates were distilled under vacuum until total volume became approximately 2.5 L/kg. Water (10 kg/kg) was added, and the crude was distilled under vacuum until total volume became approximately 2.5 L/kg. The crude was heated to 70° C. Brine (25 wt %, 9.0 kg/kg) was added, and the resulting crude was agitated for 6 h at 70° C. After cooling down to 0° C., the crude was further aged for 6 h. Product was isolated by filtration. The cake was washed with brine (pre-cooled to 0° C., 25 wt %, 2.0 kg/kg), and dried under vacuum at 45° C. Compound 7 was isolated in 99 AP and 88% yield.

Preparation of Compound 13

Step 1: Preparation of Compound 11 and Compound 12

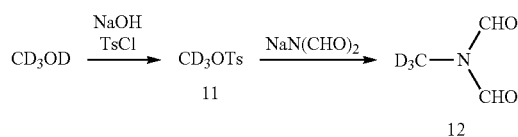

To a glass-lined reactor flushed with nitrogen were charged water (16.3 L/kg) and sodium hydroxide (3.3 kg, 3.0 equiv). The mixture was aged till sodium hydroxide reached full dissolution. The crude was cooled to 0° C. $d_4$-Methanol (1.0 kg) and THF (4.5 L/kg) were charged. A solution of TsCl (6.3 kg, 1.2 equiv) in THF (6.3 kg, 7.1 L/kg) was added over the course of 2 h. The crude was agitated at 0° C. until reaction reached completion. The batch was warmed to 20° C. The layers were separated. The collected organic layer was diluted with MTBE (4.0 kg, 5.4 L/kg), washed with brine twice (25 wt %, 4.0 kg followed by 12 kg). The organic layer was distilled under vacuum until total volume became approximately 10 L/kg. Two put/take distillations with ACN (2×10 L/kg) were undertaken for azeotropic drying. The crude was cooled to 20° C. ACN (10.0 kg, 12.8 L/kg) and NaN(CHO)$_2$ (3.3 kg, 1.2 equiv.) were added. The crude was heated to 65° C. and agitated until reaction reached completion. After cooling down to 5° C., the mixture was filtered, and the crude cake was washed with ACN twice (2×2.5 kg, 2×3.2 L/kg). The combined filtrates were distilled under vacuum until total volume became approximately 3 L/kg. The crude was cooled to 20° C. Compound 12 was isolated as an oil with 80-85 wt % in 60-70% yield.

Step 2: Preparation of Example 13

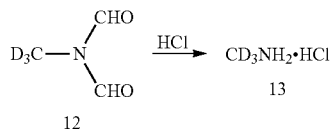

To a glass lined reactor were charged Compound 12 (1.0 kg) and methanol (3.9 kg, 5.0 L/kg) at 20° C. A solution of HCl in IPA (5-6 Normal, 4.5 kg, 1.5 equiv.) was added. The resulting mixture was heated to 50° C. and agitated until reaction reached completion. THF (10 kg, 11.2 L/kg) was added slowly and the crude was cooled to 0° C. over 2 h to afford a slurry. The product was isolated by filtration. The cake was washed with THF (3.7 kg, 4.1 L/kg), and dried under vacuum at 45° C. Compound 13 was isolated in 80% yield.

Optional Recrystallization of Compound 13:

Methanol (5.6 kg, 8.3 L/kg) and Compound 13 (1.0 kg) were charged to a glass-lined reactor. DBU (0.1 kg) was added slowly. The crude was agitated for 1 h. THF (12.4 kg, 13.9 L/kg) was added slowly, and the resulting slurry was aged for 2 h. The product was isolated by filtration. The cake was washed with THF (2.6 kg, 2.9 L/kg), and dried under vacuum at 45° C. Compound 13 was isolated in 60% yield (1$^{st}$ crop). The mother liquor was distilled under vacuum until total volume became approximately 1 L/kg. Two put/take distillations with methanol (2×2.8 kg, 2×3.6 L/kg) were performed and the solution was concentrated back to ~1 L/kg. The crude was cooled to 20° C. THF (4.8 kg, 5.4 L/kg) was added, and the resulting slurry was aged for 2 h. The product was isolated by filtration. The cake was washed with THF (1.0 kg), and dried under vacuum at 45° C. Compound 13 was isolated in 25% yield (2$^{nd}$ crop).

Example 5: Physical and Chemical Stability of Form B of Compound (I)

Samples of Form B of Compound (I) were stored at different conditions of temperature and humidity for 4 weeks. The physical stability, characterized by DSC TGA, and PXRD, were measured at 2 and 4 weeks. No change in the physical form was detected in the samples for at least 4 weeks. The data in Table 3 show that there were no measure change in chemical stability of the samples. The data in Table 4 shows longer term stability of Form B. The % shown includes values corrected for water and total volatiles resulting in greater than 100% in some cases.

TABLE 3

| | % Assay | |
|---|---|---|
| Storage Conditions | 2 weeks | 4 weeks |
| 5° C. (control) | 98.32 | |
| 5° C. | 98.31 | 98.40 |
| 25° C./60% RH (closed) | 98.26 | 98.39 |
| 40° C./75% RH (open) | 98.29 | 98.37 |
| 50° C. | 98.32 | 98.40 |
| HIL/UV | 98.44 | 98.44 |

TABLE 4

| | % Assay | | | |
|---|---|---|---|---|
| Storage Conditions | 1 Month | 3 Months | 6 Months | 12 Months |
| −20° C. | 99.9 | | | |
| 5° C. | 100.3 | 100.9 | 100.3 | 100.2 |
| 25° C./60% RH (closed) | 98.8 | 100.9 | 99.4 | 99.9 |
| 40° C./75% RH (open) | 99.8 | 98.7 | 101.0 | 100.3 |

The moisture sorption isotherm of Form B of Compound (I) is shown in FIG. 4. Form B of Compound (I) displays less than 0.5% moisture uptake between 25 to 75% relative humidity at 25° C.

Table 5 shows the results of a micro-dissolution comparative study of potential salts. This was performed due to the pH effect shown by the free base. It was shown that HCl salt mitigates the pH effect better than MSA and sulfate (SO$_4$) salts.

TABLE 5

| Form | AUC pH 2-6.5 | | AUC pH 6-6.5 | | pH-effect |
| --- | --- | --- | --- | --- | --- |
| | Mean | Std Dev | Mean | Std Dev | Ratio |
| Free Base (n = 2) | 6094.11 | 956.36 | 1640.60 | 177.60 | 0.27 |
| SO4 salt (n = 2) | 13200.71 | 530.23 | 5038.29 | 682.12 | 0.38 |
| MSA salt (n = 3) | 12045.08 | 2044.14 | 5368.76 | 2058.90 | 0.45 |
| HCl salt (n = 3) | 12345.28 | 466.47 | 7492.66 | 2303.11 | 0.61 |

Table 6 shows a Dog PK study in which the pH effect of free base vs. HCl salt at 1 mpk dose was tested. In famotidine treated dogs, the mean bioavailability of the HCl salt is 60% higher than the free base. This is consistent with the micro-dissolution pH transfer model that showed lower pH effect risk from the HCl salt as compared to the free base.

TABLE 6

PK Parameter Table

| | Dose | Cmax (ng/mL) | | Tmax | $AUC_{0-24\,h}$ (ng·h/mL) | | BA (%) | | CV |
| --- | --- | --- | --- | --- | --- | --- | --- | --- | --- |
| | (mg) | Mean | Std Dev | (h) | Mean | Std Dev | Mean | Std Dev | (%) |
| Free Base capsule(Famo) | 10 | 62.78 | 30.16 | 3.50 | 585.87 | 144.43 | 85.44 | 59.18 | 24.65 |
| Free Base capsuel (Penta) | 10 | 121.60 | 66.98 | 2.5 | 974.76 | 586.21 | 100.00 | 0.00 | 60.14 |
| HCl Salt capsule (famo) | 10 | 180.34 | 165.80 | 2 | 1339.41 | 895.81 | 160.90 | 84.97 | 66.88 |

The results showed that Form B of Compound (I) is a non-hygroscopic material, retained good potency, had no significant physical or chemical degradation, and its impurity profiles remain unchanged at the tested temperature and humidity conditions. Additionally, it provides mitigation of the pH effect versus the free base or other salt forms.

Single Crystal Data

Single crystal X-ray data was collected using a Rigaku SuperNova diffractometer, equipped with a copper anode microfocus sealed X-ray tube (CuKα) and a Dectris Pilatus3 R 200K hybrid pixel array detector. The single crystal was at room temperature (approximately 25° C.) during data collection.

The final unit cell parameters were obtained from least-squares refinement using the setting angles of 4529 reflections in the range $4.1400° < \theta < 77.1740°$. The structures were solved by direct methods using the SHELXT software and refined by full-matrix least-squares approach using the SHELXL-2014 software (Sheldrick, G. M. Acta Cryst. 2015, A71, 3-8; Sheldrick, G. M. Acta Cryst., 2008, A64, 112-122.). Structure refinements involved minimization of the function defined by $\Sigma w(|F_o|-|F_c|)^2$, where w is an appropriate weighting factor based on errors in the observed intensities, $F_o$ is the structure factor based on measured reflections, and $F_c$ is the structure factor based on calculated reflections. Agreement between the refined crystal structure model and the experimental X-ray diffraction data is assessed by using the residual factors $R=\Sigma||F_o|-|F_c||/\Sigma|F_o|$ and $wR=[\Sigma w(|F_o|-|F_c|)^2/\Sigma w|F_o|]^{1/2}$. Difference Fourier maps were examined at all stages of refinement. All non-hydrogen atoms were refined with anisotropic thermal displacement parameters. Hydrogen atoms were refined independently.

PXRD

Powder X-ray diffraction (PXRD) data were obtained using a Bruker C2 GADDS with Vantec-500 detector. The radiation was CuKα (40 KV, 40 mA). The sample-detector distance was ~20 cm. Incident optics include Goebel mirror and 0.3 mm collimator. Powder samples were placed in sealed glass capillaries of 1 mm or less in diameter: the capillary was rotated during data collection. Data were collected for $2 \leq 2\theta \leq 35°$ with a sample exposure time of at least 1000 seconds. The resulting two-dimensional diffraction arcs were integrated to create a traditional 1-dimensional PXRD pattern with a step size of 0.05 degrees 2θ in the range of ~2 to ~30 degrees 2θ.

DSC

Differential scanning calorimetry (DSC) experiments were performed in a TA Instruments™ model Q2000. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA

Thermal gravimetric analysis (TGA) experiments were performed in a TA Instruments™ model Q5000. The sample (about 10-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

Moisture-Sorption Isotherms

Moisture sorption isotherms were collected in a TA Instrument VTI-SA+ Vapor Sorption Analyzer using approximately 10 mg of sample. The sample was dried at 60° C. until the loss rate of 0.0005 wt %/min was obtained for 10 minutes. The sample was tested at 25° C. and 3 or 4, 5, 15, 25, 35, 45, 50, 65, 75, 85, and 95% RH. Equilibration at each RH was reached when the rate of 0.0003 wt %/min for 35 minutes was achieved or a maximum of 600 minutes.

ssNMR

Carbon-13 cross polarization magic angle spinning (CP-MAS) solid-state NMR (ssNMR) experiments were conducted on a Bruker AV III instrument operating at a proton frequency of 400.13 MHz. Solid samples were spun at 13 kHz in a 4 mm $ZrO_2$ rotor. The contact time was 2 milliseconds and was ramped on the proton channel from 50 to 100% (A. E. Bennett et al, *J. Chem. Phys.,* 1995, 103, 6951), (G. Metz, X. Wu and S. O. Smith, *J. Magn. Reson. A.,* 1994, 110, 219-227). The relaxation delay was maintained at $5 \times {}^1H$ $T_1$ of API, which was 16 seconds. Proton decoupling was applied using a TPPM sequence with a 3.8 microsecond pulse (66 kHz nominal bandwidth). The spectral sweep width was 300 ppm centered at 100 ppm. 2972 data points were acquired (giving a digital resolution of 20 Hz) and zero filled to 8192 prior to apodization with 20 Hz line broadening. 3072 free induction decays were co-added. The spectra were referenced indirectly to TMS using 3-methylglutaric acid (D. Barich, E. Gorman, M. Zell, and E. Munson, *Solid State Nuc. Mag. Res.*, 2006, 30, 125-129). Approximately 70 mg of sample was used for each experiment. The temperature was set to 280° K.

What is claimed is:

1. A method of preparing crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, comprising:
  (a) mixing 51 milligrams of Compound (I), which is 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, and 0.5 mL of 0.25 M HCl into 2 mL of IPA, thereby forming a mixture;
  (b) heating and stirring the mixture; and
  (c) stirring the mixture without heating,
  to obtain crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide.

2. The method according to claim 1, wherein the heating and stirring in (b) is performed at 55° C.

3. Crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide produced by the method according to claim 1, having a purity of greater than 90 wt %.

4. A method of preparing crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, comprising:
  (a) forming a solution by mixing 550 milligrams of Compound (I), which is 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, into 35 mL of THF and 2 mL of water;
  (b) adding 108 microliters of 37% HCl to the solution, thereby forming a first slurry;
  (c) drying the first slurry to obtain a solid;
  (d) suspending the solid in 5 mL of BuOAc, thereby forming a second slurry;
  (e) aging the second slurry to obtain an aged slurry;
  (f) filtering the aged slurry to obtain a wet cake; and
  (g) drying the wet cake,
  to obtain crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide.

5. The method according to claim 4, wherein the suspending in (d) is performed at 60° C., and wherein the aging in (e) is performed at 60° C.

6. The method according to claim 4, wherein the drying in (g) is performed at a temperature of from 50° C. to 60° C.

7. Crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide produced by the method according to claim 4, having a purity of greater than 90 wt %.

8. A method of preparing crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, comprising:
  (a) forming a solution by mixing 2 grams of Compound (I), which is 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, and 15 mL of DMA;
  (b) forming an HCl solution by mixing 395 microliters of 37% HCl, 25 mL of BuOAc, and 7.6 mL of DMA;
  (c) adding, to the solution formed in (a), the following:
    (i) 3 mL of the HCl solution;
    (ii) 40 mg of Compound (I) Form B seeds; and
    (iii) the remaining HCl solution, thereby forming a slurry;
  (d) cooling the slurry;
  (e) stirring the slurry;
  (f) further cooling the slurry, followed by further stirring the slurry;
  (g) filtering the slurry to obtain a wet cake;
  (h) washing the wet cake with 6 mL of BuOAc; and
  (i) drying the wet cake,
  to obtain crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide.

9. The method according to claim 8, wherein forming the solution in (a) is performed at 60° C., and wherein forming the HCl solution in (b) is performed at 60° C.

10. The method according to claim 8, wherein adding the remaining HCl solution in (e) is performed over a time period of at least 3 hours.

11. The method according to claim 8, wherein in (d), the slurry is cooled from 60° C. to 50° C., over a time period of 1 hour.

12. The method according to claim 8, wherein the stirring in (e) is performed at 50° C. for at least 15 hours.

13. The method according to claim 8, wherein the further cooling in (f) is performed by cooling the slurry to 20° C., over a time period of 1 hour.

14. The method according to claim 8, wherein in (i), the wet cake is dried in a vacuum oven at a temperature of 50° C.

15. Crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide produced by the method according to claim 8, having a purity of greater than 90 wt %.

16. A method of preparing crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, comprising:
  (a) forming a solution by combining 1.4 kilograms of Compound (I), which is 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, and 8.4 liters of NMP and applying heat;
  (b) polish filtering the solution, thereby obtaining a polish filtered solution;
  (c) heating the polish filtered solution and adding 0.421 kilograms of HCl 37 wt % solution to the polish filtered solution;
  (e) adding 14 liters of ethyl acetate to obtain a slurry;
  (f) cooling the slurry to obtain a cooled slurry;
  (g) aging the cooled slurry to obtain an aged slurry;
  (h) filtering the aged slurry to obtain a wet cake; and
  (i) drying the wet cake,
  to obtain crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide.

17. The method according to claim 16,
wherein the applying heat in (a) is performed at 50° C.,
wherein the polish filtering in (b) is performed at 50° C., and
wherein in (c), the polish filtered solution is heated to 50° C.

18. The method according to claim 16, wherein in (f), the slurry is cooled to 20° C., over a time period of 1 hour.

19. The method according to claim 16, wherein in (g), the cooled slurry is aged for 12 hours.

20. The method according to claim 16, further comprising washing the wet cake obtained in (h) with ethyl acetate.

21. The method according to claim 16, wherein in (i), the wet cake is dried in a vacuum oven at a temperature of 55° C.

22. Crystalline Form B of 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide produced by the method according to claim 16, having a purity of greater than 90 wt %.

23. A method of preparing crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, comprising:
(a) forming a solution by combining 2.323 kilograms of Compound (I), which is 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, and 16.26 liters of NMP and applying heat;
(b) polish filtering the solution, thereby obtaining a polish filtered solution;
(c) heating the polish filtered solution and adding 0.55 kilograms of HCl 37 wt % solution to the polish filtered solution;
(e) adding 0.04 kilograms of Compound (I) Form B seeds and 0.47 liters of ethyl acetate to obtain a slurry;
(f) aging the slurry to obtain a first aged slurry;
(g) adding 13.48 liters of ethyl acetate to the first aged slurry;
(h) further aging the first aged slurry to obtain a second aged slurry;
(i) cooling the second aged slurry to obtain a cooled slurry;
(j) aging the cooled slurry to obtain a third aged slurry;
(k) filtering the third aged slurry to obtain a wet cake; and
(l) drying the wet cake,
to obtain crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide.

24. The method according to claim 23,
wherein the applying heat in (a) is performed at 50° C.,
wherein the polish filtering in (b) is performed at 50° C., and
wherein in (c), the polish filtered solution is heated to 50° C.

25. The method according to claim 23, wherein in (f), the slurry is aged for 90 minutes.

26. The method according to claim 23, wherein in (h), the first aged slurry is further aged for 60 minutes at a temperature of 50° C.

27. The method according to claim 23, wherein in (i), the second aged slurry is cooled to 20° C., over a time period of 1 hour.

28. The method according to claim 23, wherein in (j), the cooled slurry is aged for 12 hours.

29. The method according to claim 23, further comprising washing the wet cake obtained in (k) with ethyl acetate.

30. The method according to claim 23, wherein in (l), the wet cake is dried in a vacuum oven at a temperature of 65° C.

31. Crystalline Form B of 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide produced by the method according to claim 23, having a purity of greater than 90 wt %.

32. A method of preparing crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, comprising:
(a) forming a solution by combining Compound (I), which is 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, and NMP and applying heat;
(b) polish filtering the solution, thereby obtaining a polish filtered solution;
(c) heating the polish filtered solution and adding an HCl solution to the polish filtered solution;
(e) adding ethyl acetate to obtain a slurry;
(f) cooling the slurry to obtain a cooled slurry;
(g) aging the cooled slurry to obtain an aged slurry;
(h) filtering the aged slurry to obtain a wet cake; and
(i) drying the wet cake,
to obtain crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide;
wherein crystalline Form B of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide is characterized by one or more of the following:
(i) a powder x-ray diffraction (PXRD) pattern comprising four or more 2θ values in degrees (CuKα) selected from: 8.1±0.2; 8.9±0.2; 10.4±0.2; 12.8±0.2; 14.9±0.2; 16.4±0.2 and 18.4±0.2, wherein the PXRD pattern of Form B is measured at a temperature of about 25° C.;
(ii) a powder x-ray diffraction (PXRD) pattern comprising the 2θ values in degrees (CuKα) at 8.1±0.2 and 12.8±0.2, and three or more 2θ values in degrees (CuKα) selected from: 8.9±0.2; 10.4±0.2; 14.9±0.2; 16.4±0.2 and 18.4±0.2, wherein the PXRD pattern of Form B is measured at a temperature of about 25° C.;
(iii) an observed powder x-ray diffraction pattern substantially as shown in FIG. 1;
(iv) unit cell parameters substantially equal to the following:
a=8.55±0.05 Å
b=11.60±0.05 Å
c=12.00±0.05 Å
α=114.3±0.5°
β=94.1±0.50
γ=93.31±0.50
Space group: P-1
Molecules per unit cell (Z): 2
wherein the unit cell parameters of Form B are measured at a temperature of about 25° C.

* * * * *

UNITED STATES PATENT AND TRADEMARK OFFICE
CERTIFICATE OF CORRECTION

PATENT NO. : 11,613,529 B2
APPLICATION NO. : 17/058698
DATED : March 28, 2023
INVENTOR(S) : Daniel Roberts et al.

Page 1 of 2

It is certified that error appears in the above-identified patent and that said Letters Patent is hereby corrected as shown below:

On the Title Page

<u>In the Abstract:</u>

Column 2, Abstract, Line 2, delete "methy" and insert -- methyl --.

Column 2, Abstract, Line 3, delete "N-methyl-d3)" and insert -- N-(methyl-$d_3$) --.

In the Claims

Column 21, Claim 4, Line 39, delete "THE" and insert -- THF --.

Column 22, Claim 16, Lines 59-63, delete
"(e) adding 14 liters of ethyl acetate to obtain a slurry;
(f) cooling the slurry to obtain a cooled slurry;
(g) aging the cooled slurry to obtain an aged slurry;
(h) filtering the aged slurry to obtain a wet cake; and
(i) drying the wet cake," and insert
-- (d) adding 14 liters of ethyl acetate to obtain a slurry;
(e) cooling the slurry to obtain a cooled slurry;
(f) aging the cooled slurry to obtain an aged slurry;
(g) filtering the aged slurry to obtain a wet cake; and
(h) drying the wet cake, --.

Column 23, Claim 23, Lines 35-46, delete
"(e) adding 0.04 kilograms of Compound (I) Form B seeds and 0.47 liters of ethyl
acetate to obtain a slurry;
(f) aging the slurry to obtain a first aged slurry;
(g) adding 13.48 liters of ethyl acetate to the first aged slurry;
(h) further aging the first aged slurry to obtain a second aged slurry;

Signed and Sealed this
Seventh Day of November, 2023

Katherine Kelly Vidal
*Director of the United States Patent and Trademark Office*

CERTIFICATE OF CORRECTION (continued)
U.S. Pat. No. 11,613,529 B2

(i) cooling the second aged slurry to obtain a cooled slurry;
(j) aging the cooled slurry to obtain a third aged slurry;
(k) filtering the third aged slurry to obtain a wet cake; and
(l) drying the wet cake," and insert
-- (d) adding 0.04 kilograms of Compound (I) Form B seeds and 0.47 liters of ethyl acetate to obtain a slurry;
(e) aging the slurry to obtain a first aged slurry;
(f) adding 13.48 liters of ethyl acetate to the first aged slurry;
(g) further aging the first aged slurry to obtain a second aged slurry;
(h) cooling the second aged slurry to obtain a cooled slurry;
(i) aging the cooled slurry to obtain a third aged slurry;
(j) filtering the third aged slurry to obtain a wet cake; and
(k) drying the wet cake, --.

Column 24, Claim 32, Lines 25 - 29, delete
"(e) adding ethyl acetate to obtain a slurry;
(f) cooling the slurry to obtain a cooled slurry;
(g) aging the cooled slurry to obtain an aged slurry;
(h) filtering the aged slurry to obtain a wet cake; and
(i) drying the wet cake," and insert
-- (d) adding ethyl acetate to obtain a slurry;
(e) cooling the slurry to obtain a cooled slurry;
(f) aging the cooled slurry to obtain an aged slurry;
(g) filtering the aged slurry to obtain a wet cake; and
(h) drying the wet cake, --.

Column 24, Claim 32, Line 59, delete "0.50" and insert -- 0.5° --.

Column 24, Claim 32, Line 60, delete "0.50" and insert -- 0.5° --.